United States Patent [19]
Elstrom et al.

[11] Patent Number: 5,913,833
[45] Date of Patent: Jun. 22, 1999

[54] METHOD AND APPARATUS FOR OBTAINING BIOLOGICAL FLUIDS

[75] Inventors: Tuan A. Elstrom, Lake Bluff; Eric B. Shain, Glencoe, both of Ill.

[73] Assignee: Abbott Laboratories, Abbott Park, Ill.

[21] Appl. No.: 08/798,403

[22] Filed: Feb. 7, 1997

[51] Int. Cl.$^6$ .................................................. A61B 5/00
[52] U.S. Cl. ........................... 600/573; 604/22; 604/290
[58] Field of Search .................................. 600/562, 573, 600/576, 578, 579; 604/19, 22, 289, 290, 313

[56] References Cited

U.S. PATENT DOCUMENTS

| | | |
|---|---|---|
| 4,708,127 | 11/1987 | Abdelghani . |
| 4,767,402 | 8/1988 | Kost et al. . |
| 4,780,212 | 10/1988 | Kost et al. . |
| 4,787,888 | 11/1988 | Fox . |
| 4,821,740 | 4/1989 | Tachibana et al. . |
| 4,948,587 | 8/1990 | Kost et al. . |
| 4,953,565 | 9/1990 | Tachibana et al. . |
| 5,007,438 | 4/1991 | Tachibana et al. . |
| 5,016,615 | 5/1991 | Driller et al. . |
| 5,076,208 | 12/1991 | Zohar et al. . |
| 5,115,805 | 5/1992 | Bommannan et al. . |
| 5,147,291 | 9/1992 | Cukier . |
| 5,171,215 | 12/1992 | Flanagan . |
| 5,222,937 | 6/1993 | Kagawa ................................. 604/22 |
| 5,231,975 | 8/1993 | Bommannan et al. . |
| 5,267,985 | 12/1993 | Shimada et al. . |
| 5,323,769 | 6/1994 | Bommannan et al. . |
| 5,405,614 | 4/1995 | D'Angelo et al. . |
| 5,415,629 | 5/1995 | Henley . |
| 5,421,816 | 6/1995 | Lipkovker . |
| 5,437,606 | 8/1995 | Tsukamoto . |
| 5,445,611 | 8/1995 | Eppstein et al. . |
| 5,458,140 | 10/1995 | Eppstein et al. . |

FOREIGN PATENT DOCUMENTS

| | | |
|---|---|---|
| 0625360 | 11/1994 | European Pat. Off. . |
| 0736305 | 10/1996 | European Pat. Off. . |
| 9408655 | 4/1994 | WIPO . |
| 9800194 | 1/1998 | WIPO . |

OTHER PUBLICATIONS

Brown, L. and Langer, R.; "Transdermal Delivery of Drugs", *Ann. Rev. Med.*, vol. 39, pp. 221–229 (1988).

ter Haar, G. R. and Daniels, S.; "Evidence for ultrasonically induced cavitation in vivo", *Phys. Med. Biol.*, vol. 26, NO. 6, pp. 1145–1149 (1981).

Levy, D. et al; "Effect of Ultrasound on Transdermal Drug Delivery to Rats and Guinea Pigs", *J. Clin. Invest.*, vol. 83, pp. 2074–2078 (Jun. 1989).

*Primary Examiner*—Max Hindenburg
*Attorney, Agent, or Firm*—David L. Weinstein

[57] ABSTRACT

This invention provides a method and apparatus for disrupting the outermost layer of skin, the stratum corneum, to provide access to biological fluid, which can then be used to determine the concentration of glucose in blood. The invention can be used to extract interstitial fluid, blood, and mixtures of interstitial fluid and blood from the body of a human or an animal.

The method comprises the steps of (1) attaching a receptacle for collecting biological fluid to the surface of the skin of a patient, (2) introducing an oscillation concentrator attached to an oscillation element into the receptacle, (3) positioning the oscillation concentrator at a desired distance from the surface of the skin, (4) activating the oscillation element to transversely oscillate the attached oscillation concentrator, (5) collecting the biological fluid after a specific period of time, and (6) analyzing the biological fluid for the presence of an analyte.

19 Claims, 2 Drawing Sheets

FIG. 2

METHOD AND APPARATUS FOR OBTAINING BIOLOGICAL FLUIDS

BACKGROUND OF THE INVENTION

1. Field of the Invention

This invention relates to the field of collection of biological fluids for diagnostic purposes. More particularly, the invention relates to the use of energy provided by an oscillating element to enhance the transdermal transport of biological fluids through human or animal skin.

2. Discussion of the Art

The prevalence of diabetes has been increasing markedly in the world.

At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally insert the blood-coated strip into a blood glucose meter for measurement of glucose concentration by determination of change in reflectance.

There are numerous devices currently available for diabetics to monitor the level of blood glucose. The best of these devices require the diabetic to prick a finger and to collect a drop of blood for placement on a strip, which is inserted into a monitor that determines the level of glucose in the blood. Pricking one's finger tends to be painful. Moreover, a relatively large wound is produced by the pricking device, typically a lancet or a needle. It is known that the pain arising from the finger prick deters diabetics from compliance with the monitoring regimen. Lack of compliance increases the risk of complications due to diabetes. Thus there is a need for a more painless and less traumatic means of collecting biological samples for monitoring one's level of glucose in blood.

Ultrasound has been used to enhance the transdermal transport of biological fluids through human or animal skin. Eppstein et al, U.S. Pat. No. 5,458,140, discloses a method of enhancing the permeability of the skin or mucosa to an analyte for diagnostic purposes utilizing ultrasound or ultrasound plus a chemical enhancer. The ultrasound may be modified by means of frequency modulation, amplitude modulation, phase modulation, and/or combinations thereof. Lipkovker, U.S. Pat. No. 5,421,816, discloses a noninvasive method of withdrawing a fluid from an organism and determining the concentration of a substance in the fluid, said method comprising the steps of: (a) creating a cavity juxtaposed against the skin of said organism; (b) applying a focused beam of ultrasonic energy to the skin of said organism in the region of said cavity to cause fluid to be withdrawn into said cavity; and (c) analyzing fluid withdrawn into said cavity.

SUMMARY OF THE INVENTION

This invention provides a method and apparatus for disrupting the outermost layer of skin, the stratum corneum, to provide access to biological fluid, which can then be used to determine the concentration of glucose in blood. The invention can be used to extract interstitial fluid, blood, and mixtures of interstitial fluid and blood from the body of a human or an animal.

The method comprises the steps of (1) attaching a receptacle for collecting biological fluid to the surface of the skin of a patient, (2) introducing an oscillation concentrator attached to an oscillation element into the receptacle, (3) positioning the oscillation concentrator at a desired distance from the surface of the skin, (4) activating the oscillation element to transversely oscillate the attached oscillation concentrator, (5) collecting the biological fluid after a specific period of time, and (6) analyzing the biological fluid for the presence of an analyte.

The receptacle can contain a coupling medium when the desired bodily fluid is interstitial fluid. The receptacle need not contain a coupling medium when the desired biological fluid is blood. The oscillation concentrator can be a needle or a wire, but is not limited to these specific embodiments. The oscillation element can be an ultrasonic horn or a piezoelectric transducer, but is not limited to these specific embodiments.

In a preferred embodiment, the apparatus comprises a needle having a proximal end and a distal end, and having an electro-mechanical transducer, such as a piezoelectric crystal, attached at its proximal end. The electro-mechanical transducer is excited by voltage and is caused to vibrate. Subsequently, the vibration is transferred to the needle, thereby causing transverse displacement of the distal end of the needle. When a piezoelectric crystal is used as the electro-mechanical transducer, the voltage applied via electrodes attached to the piezoelectric crystal causes the crystal to expand and contract in synchrony with the source of excitation. The expansion and contraction of the crystal attached to a needle causes the needle to vibrate. The needle is immersed in a receptacle, e.g., a reservoir, containing a coupling medium, preferably a liquid, in such a manner that the coupling medium is in contact with the surface of human or animal skin. The coupling medium allows for the transfer of mechanical waves, preferably ultrasonic waves, or hydrodynamic stress to the skin. The distal end of the needle can be positioned at a range of distances from the surface of the skin, from touching the skin to a few millimeters from the surface of the skin. When in transverse vibration, the distal end of the needle produces mechanical waves and hydrodynamic stress, depending on its distance from the skin. The amount of stress is determined by the maximum displacement of the distal end of the needle. The mechanical waves and hydrodynamic stress bring about disruption of the outermost layer of human or animal skin, the stratum corneum.

The method of disrupting the stratum corneum provides a minimally invasive, substantially painless, means of sampling human transudate. The method and apparatus of this invention can provide a diabetic with the incentive to comfortably monitor his level of blood glucose at any time.

DETAILED DESCRIPTION

As used herein, the term "needle" means an elongated element having an aspect ratio, i.e., ratio of length to largest cross-sectional dimension, of at least about 100:1. The expression "transverse oscillation" means that the individual molecules of which the needle is comprised move in a cyclic motion in a direction perpendicular to the long axis of the needle. The resultant motion is analogous to the motion exhibited by water waves produced by large bodies of water, such as the ocean. Transverse oscillation is also exhibited by springboards after a diver has jumped from the end of the board into a swimming pool. The expression "transverse oscillating needle" means a needle undergoing transverse oscillation. The transverse oscillating needle is capable of converting an ultrasonic wave at a specific frequency into many traveling waves as it propagates along the needle. The expression "ultrasonic wave" means a mechanical wave having a frequency of oscillation in the range of 20 kHz and above.

The expression "hydrodynamic stress" means the stress generated by a flowing fluid at a boundary. A flowing fluid usually flows within a confined region of space, such as, for example, a pipe. The flowing fluid usually interacts with the surface of the confined space as it flows. The interface between the flowing fluid and the surface of the confined space is called the boundary or boundary layer.

The expression "dispersive medium" means a medium that distributes energy in different directions, angles, or forms.

The expression "standing wave" means a wave that does not move or propagate. The peaks and troughs of the wave are an integer-multiple number of half-wavelengths apart. A standing wave is produced by the interference of two or more waves that possess phases that add constructively or destructively by integer-multiple number of half-wavelengths, e.g., 1/2 wavelength, 2/2 wavelength, 3/2 wavelength. A plurality of waves emanating from a transverse oscillating needle can produce standing waves within the medium of propagation by having the appropriate phases. The expression "plane traveling wave" means a wave having a wave front of relatively the same dimension as the greatest dimension of the source that produced the wave. It propagates with a relatively flat wave front perpendicular to the direction of its propagation.

The term "microstreaming" means fluid motion arising from the propagation of acoustic waves within a physical boundary. The expression "velocity gradient" means a change in fluid motion as a function of distance from the needle.

The term "probe" means a tip of a sonicator horn used for disruption of cells. The term "booster" means an added portion of a sonicator horn that serves to increase the amplitude of oscillation displacement. The term "amplitude" means the magnitude of the extent or range of motion. The expression "three axis" means capable of moving in three directions.

In general, the method of this invention comprises the steps of (1) attaching a receptacle for collecting biological fluid to the surface of the skin of a patient, (2) introducing an oscillation concentrator attached to an oscillation element into the receptacle, (3) positioning the oscillation concentrator at a desired distance from the surface of the skin, (4) activating the oscillation element to transversely oscillate the attached oscillation concentrator, (5) collecting the biological fluid after a specific period of time, and (6) analyzing the bodily fluid for the presence of an analyte.

The receptacle can contain a coupling medium when the desired biological fluid is interstitial fluid. The receptacle need not contain a coupling medium when the desired biological fluid is blood. The coupling medium can be an aqueous or non-aqueous liquid. The coupling medium allows the efficient transfer of acoustic energy from the oscillation concentrator to the skin. The coupling medium should have an acoustic impedance similar to that of skin. Coupling media suitable for this invention include, but are not limited to, aqueous saline solution and sodium dodecyl sulfate in aqueous saline solution. Other coupling media suitable for this invention are well-known to those of ordinary skill in the art. In the case of transdermal drug delivery, the drug of interest is dissolved in the coupling medium.

The oscillation concentrator can be a needle or wire, but is not limited to these specific embodiments. The needle may be cylindrical in shape. It can also have a conical tip, hemispherical tip, or a tip of any other shape suitable for providing mechanical waves. The tip of the needle may be pointed or blunt. The tip of the needle is alternately referred to herein as the distal end of the needle. The needle may be made from stainless steel, tungsten, copper, or any other material having sufficient mechanical strength for the purpose of this invention. The needle may be stiff or flexible. The parameters of the needle can be optimized by trial-and-error relatively easily by one of ordinary skill in the art.

The oscillation element can be ultrasonic horn or a piezoelectric transducer, but is not limited to these specific embodiments.

A transverse oscillating needle acts as dispersive medium for mechanical waves. A transverse oscillating needle can produce a plurality of waves with frequencies ranging from about $1 \times 10^2$ cycles per second to about $1 \times 10^9$ cycles per second, preferably from about $1 \times 10^4$ cycles per second to about $1 \times 10^7$ cycles per second, when excited at an appropriate mode. A mode, or normal mode, of motion is a motion in which each particle making up the oscillator moves sinusoidally with the same frequency. An appropriate mode is a mode that is conducive to producing the desired frequency.

The plurality of waves will penetrate to various depths of the skin, including the deeper portions of the epidermis and dermis. The constructive and destructive interference produced by traveling waves converts the traveling waves emanating and penetrating the skin into a standing wave. A standing wave produces forces that can displace cells such as stratum corneum cells from equilibrium. Such displacement of cells are essentially cracks in the barrier, e.g., stratum corneum, thereby providing formation of pores. The thus-formed pores provide enhancement of transdermal transport necessary for sampling human transudate or delivery of materials, e.g., drugs, through skin.

Transdermal transport is enhanced by both the action of the viscous stress that disrupts the stratum corneum, e.g., forms one or more pores in the stratum corneum, and the microstreaming that brings about convective transfer of fluid. The creation of a standing wave within skin can cause cellular movements as well as microstreaming of extracellular fluid. This fluid mechanical behavior can provide a means for the enhancement of transdermal transport of materials through the skin. The physical effects are cellular displacement from equilibrium and convective motion due to the propagation of acoustic energy within the extracellular space of the skin. Cellular displacement provides a temporary breakdown of the stratum corneum. In the absence of cellular displacement, the stratum corneum prevents interstitial fluid from leaking out of the skin. Convective motion provides the motive force for flow of interstitial fluid and glucose out of the skin. This motive force exceeds the forces that give rise to transdermal diffusion. The cellular displacement occurs due to the compression and decompression caused by the presence of an acoustic field. The cellular structure of the skin undergoes compression and decompression as the wave propagates through the skin. The convective motion is caused by the presence of the acoustic field. The convective motion results from the time-independent property of an acoustic field. In other words, the acoustic property, e.g., convective motion or microstreaming, is a property of the acoustic field that is independent of time.

The method of this invention wherein a transverse vibrating needle is employed differs from the methods of the prior art in a number of ways. In the prior art, conventional means of producing ultrasonic waves are used. These conventional means require the use of a piezoelectric element to convert electric energy into mechanical energy that propagates from the piezoelectric element into another medium, such as a metallic horn or an acoustic lens. The mode of propagation of a wave is longitudinal where the medium of propagation, e.g., a horn, used to match impedance with the medium to be excited, e.g., the skin, is put into compression and decompression along the long-axis of the direction of propagation. The oscillating motion of the medium resembles the motion of an accordion. The waves produced are usually of a specific frequency and can only be a given specific frequency at a given time. The waves are considered plane traveling waves.

The wave equation describing the propagation of acoustic waves does not apply to a metallic cylinder, such as a needle, made to vibrate in transverse mode, because the propagation of the waves is dependent on the fourth derivative of the displacement with respect to distance. The transverse oscillation is analogous to the motion of a diving board after the diver has left the board. The motion is also analogous to the movement of a tuning fork after it has been struck.

Another major difference from the prior art is that fluid such as diluted blood or transudate can be collected with a transverse vibrating needle.

Collection of these fluids can be carried out when the needle is in contact with the skin. The vibration of the needle assists in the dilution or collection of blood or transudate into the reservoir. This mode of operation can ideally function without any discomfort when the needle is in contact with the skin of a patient.

A transverse oscillating needle provides a plurality of waves to propagate along and out of the distal end of the needle. In this mode, the needle acts as a dispersive medium, because it can be excited at one end with one specific excitation frequency, yet has the ability to produce a complex mixture of a plurality of waves having different frequencies. The needle also has the ability to attract species of relevant molecules, such as proteins, glucose, and the like that are present in a liquid medium due to its ability to create velocity gradients in the liquid medium, coupling medium, and the cellular region of the skin near the distal end of the needle. These velocity gradients are sufficiently strong to lyse cells disposed within a few microns of the distal end of the needle. The cells are lysed by the mechanical stress generated at the region near the distal end of the needle. A cell membrane has a threshold for structural integrity, thereby serving as a container of the cell's contents. When that structural strength is exceeded by forces acting on it, such as pressure, or force per unit area, the cell membrane breaks and the cell bursts. At the distal end of the needle, the oscillation creates enough pressure to burst or lyse cells. Once the stratum corneum is disrupted, the needle also provides a mean attraction of fluid or species within the fluid. The needle provides attraction in the sense that fluid flow caused by a transverse oscillator is in circular motion from toward the distal end of the needle to away from the distal end of the needle. During the one cycle of fluid flow, fluid elements and materials within a fluid will flow toward the distal end of the needle. In the context of glucose extraction, some of the fluid will flow toward the distal end of the needle and in the process of doing so will mix with the coupling medium. The needle can be made to oscillate at low power, and thus is more efficient in comparison to conventional transducers, thereby minimizing heating. The needle acts as a self focuser due to its rather small radius, i.e., the needle, due to its sharp end, can be used to localize the application of the acoustic field. This is desirable when only a small area of exposure is required for disruption. Conventional means for focusing ultrasound to a small spot require lenses that can be significantly thick at frequencies of hundreds of kilohertz. Alignment of the distal end of the needle to a specific spot on the skin is easier than aligning a focused acoustic beam that is usually invisible to the naked eye.

An important advantage of the method of this invention over methods of the prior art is that material comes out of the skin when the needle is positioned near the surface of the skin though a liquid coupling medium. Glucose present in the mixture can be analyzed using High Pressure Liquid Chromatography (HPLC). When the needle is touching the skin, certain biological fluids can be made to come out of the body and into the coupling medium. The nature of the fluid that comes out depends on the proximity of the distal end of the needle to the surface of the skin. The action of the needle does not cause any discomfort at certain distances from the skin but is still able to provide disruption of the stratum corneum. The disruption is not visible to the naked eye.

The method of this invention can be used to cause disruption of the stratum corneum, thereby allowing movement of human metabolites from within skin to the outside of the body. Once the metabolites cross the disrupted stratum corneum and are accumulated in a reservoir adjacent to the skin, they can be quantified using a variety of sensors.

This invention can be used for the minimally invasive detection of glucose for diabetes health management. The method and apparatus of this invention can provide a substantially painless and less intrusive means of sampling human metabolites, such a glucose, relative to the current practice. The transverse oscillating needle can be combined with biosensors to provide a variety of structures analogous to glucose meters currently available to diabetics. A product analogous to a wrist watch can contain a portion for sampling and a portion for insulin or drug delivery, thereby creating a closed-loop device.

The following examples are illustrative of the invention and are not to be interpreted as limiting the scope of the invention, as defined in the claims.

EXAMPLE I

Figures 1, 3:
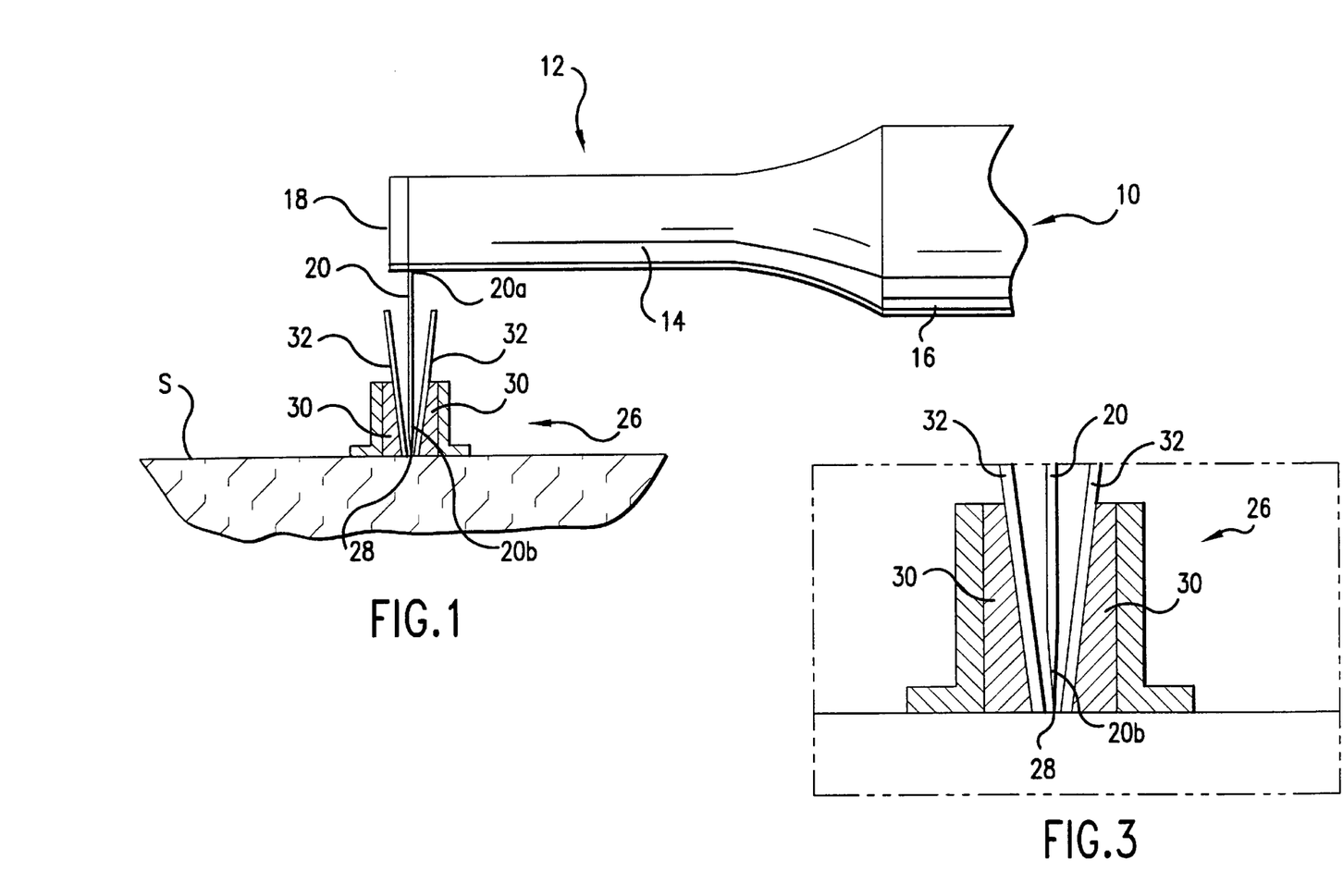
FIG. 1 is an elevational view of an embodiment of an apparatus suitable for carrying out the method of the present invention. The view of the receptacle component is in cross-section.
FIG. 3 is an enlarged cross-sectional view of the receptacle component and needle of the embodiment shown in FIG. 1.
Figure 2:
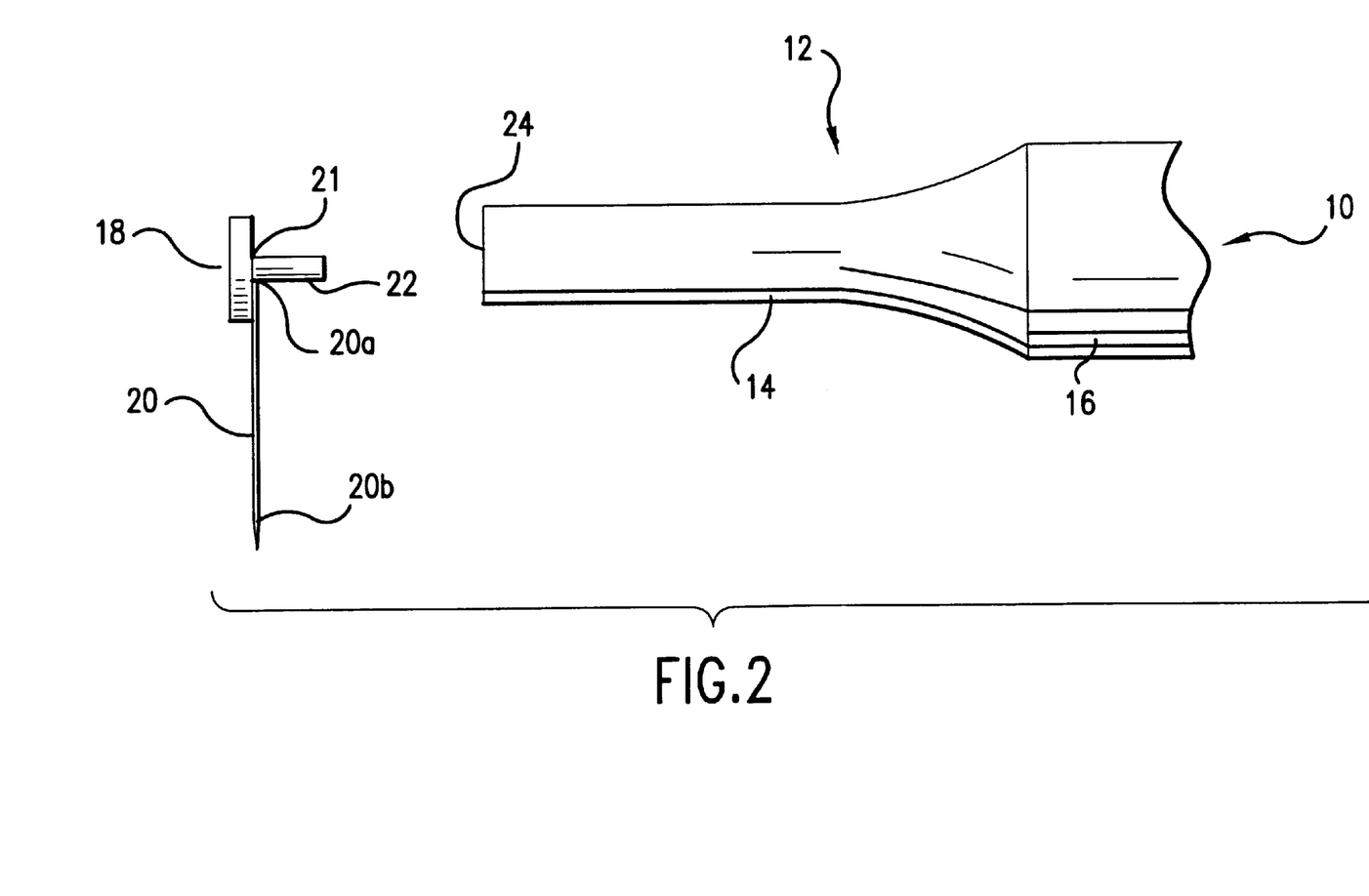
FIG. 2 is a partially exploded elevational view of a portion of the embodiment shown in FIG. 1.

Referring now to FIGS. 1, 2, and 3, the invention can be demonstrated by an apparatus 10 that employs a sonicator horn 12 available from Sonics and Materials, Danbury, Conn. Model VCX 400. The sonicator horn 12 has a tapered probe 14 having a diameter of 13 mm. The probe 14 is attached to a booster 16. The 13 mm diameter probe 14 has a replaceable tip 18 having a shape similar to that of a screw. The replaceable tip 18, Order #630-0406, is used as a means for attaching a needle 20 to the probe 14. The needle 20 has a proximal end 20a and a distal end 20b. The long axis of the attached needle 20 is disposed perpendicular to the axis of the probe 14. Attachment of the needle 20 to the probe 14 is effected by forming a hole 21 having a diameter comparable to the diameter of the needle 20 perpendicular to the shaft 22 of the replaceable tip 18. The location of the hole should be sufficiently precise so as to sandwich the needle 20 between the tip 18 and the probe 14 when the tip 18 is screwed flush with the face 24 of the probe 14. A beading needle size 10/13 assisted, manufactured by DMC, South Kearny, N.J., available at Woolworth's, Lake Forest, Ill., can be placed into the hole 21 of the replaceable tip 18 and screwed into place to be flush with the face 24 of the probe 14. The VCX 400 sonicator horn 12 is equipped with a power supply (not shown) capable of delivering a range of amplitudes to the probe 14. The amplitude is measured by the magnitude of the voltage signal delivered to the crystal contained within the horn 12. The probe 14 also has indicators that provide a reading of the power delivered to the piezoelectric crystals used to excite the probe 14. The power supply has indicators that provide an indication of the amount of power delivered to the horn 12. The VCX 400 sonicator horn delivers ultrasound energy at specifically 20,000 cycles per second. It is 20,000 cycles per second motion that will be transferred to the needle 20 during operation. The operation of the needle 20 is not limited to 20,000 cycles per second. Other frequencies can be used, and 20,000 cycles per second was used for convenience.

For glucose monitoring, the probe 14 is disposed horizontally; the needle 20, when attached, should be perpendicular to the horizontal axis of the probe 14. Before the needle 20 is attached to the probe 14, the sonicator horn 12 should be tuned with the replaceable tip 18 in place as specified by Sonics and Materials. The replaceable tip 18 is then removed and the needle 20 is attached to the tip 18. The needle 20 is then lowered into a reservoir 26 that has a small orifice 28 at the interface between the reservoir 26 and the skin, designated herein by the letter "S". The reservoir 26 is disposed upon the surface of the skin of a human or an animal such that the orifice 28 is adjacent to the surface of the skin.

A convenient coupling as well as alignment arrangement involves securing the reservoir 26 onto a fixture (not shown) capable of being translated in three axes. Securing can be effected by attaching the reservoir 26 to a three-axis translation stage (not shown) by means of mechanical fasteners. The stage is mounted on a platform (not shown). The platform is located directly below the horn-needle assembly. The bottom of the reservoir 26 is accessible to a human appendage such as the forearm or the top of the wrist. The skin of the wrist or forearm can be firmly placed against the bottom of the reservoir 26 by moving the wrist or forearm upwardly against the reservoir 26.

A reservoir 26 suitable for the method and apparatus of this invention can be constructed by combining a well 30 and a micropipette tip 32. The well 30 that was used in the subsequent examples had a top portion of 8 mm outside diameter and a 5 mm inside diameter, had a height of approximately 1 cm, and had a bottom portion of 13 mm diameter and a thickness of approximately 1 mm. The micropipette tip 32 that was used in the subsequent examples was cut so as to have a small orifice 28 approximately 1 mm in diameter. The micropipette tip 32 can be adhered into the inside wall of the well 30 by means of a suitable adhesive, e.g., epoxy. The combination of the well 30 and the micropipette tip 32, referred to as the reservoir 26, is convenient for placing a small volume of fluids into the bottom of the reservoir 26.

A volume of fluid from, e.g., about 65 to about 5 microliters, is placed into the reservoir 26 adjacent to the skin. Distilled water can be used as a coupling medium. A low volume of coupling medium is desired in order to collect a higher concentration of glucose. For this example, 5 microliters of distilled water is sufficient for use with the needle 20 previously described. The needle 20 is lowered into the reservoir 26 and aligned co-axially with the orifice 28 adjacent to the skin. The specific distance of the tip, i.e., the distal end, 20b of the needle 20 from the skin is adjusted by means of the three-axis translation stage (not shown). The distal end 20b of the needle 20 should be immersed within the volume of fluid. Preferably, the distal end 20b of the needle, i.e., the distal end of the needle, is positioned at a distance ranging from about 0.1 $\mu$m to about 1000 $\mu$m from the surface of the skin. The amplitude of the power supply of the VCX 400 sonicator horn can be set at a level of from 0 to 100%, preferably 5%. The amplitude setting is dependent on the level of mechanical coupling from the tip 18 of the probe 14 to the needle 20 and to the specific point of contact of the probe 14 and needle 20. The power supply of the VCX 400 sonicator horn 12 is equipped so that the user is capable of determining the amplitude of voltage applied to the crystal in the horn 12. This amplitude subsequently defines the amount of acoustic pressure delivered to the medium of interest. The power unit provides a tuning knob to adjust the frequency of excitation of the horn, because the unit drifts daily. The unit also provides the user the capability to define the duration of excitation or exposure through an internal computer interface. This information or parameter can be stored in the memory of the computer. Good mechanical coupling of the tip 18 to the probe 14 will result in a lower amplitude requirement. An exposure duration of one minute can be programmed so as to stop the exposure of the skin to the needle 20 after one minute. The ultrasonic horn 12 can be turned on by pushing the start button. The skin is then exposed to ultrasonic waves for the period of time specified, e.g., typically for a duration of one minute. After the sonicator horn 12 shuts off the ultrasonic waves, all the fluid obtained is collected into a HPLC vial by means of a micropipette and tip. The sample is then analyzed on a HPLC ("DIONEX") for glucose.

An optimal distance from the distal end 20b of the needle 20 to the surface of the skin S is needed to extract glucose without any visible damage to the skin. The optimal distance can be determined by operating the apparatus at various distances from slightly touching the skin to a distance of 200 $\mu$m or more from the surface of the skin. It is conceivable that when the skin is coupled to the reservoir 26 by exertion of pressure that the area of the skin exposed is not in a two-dimensional plane, but that the surface of the skin bulges upward. The control of the distance from the distal end 20b of the needle 20 to the surface of the skin is affected. The degree of bulging of the skin is determined by the individual patient's skin elasticity. In order to properly determine the optimal distance for the patient, a series of runs must be performed on the patient. The needle 20 is placed as close to the surface of the skin as possible, thus drawing blood into the reservoir 26; then the needle 20 is moved away from the surface of the skin in increments of 10 $\mu$m using the three-axis stage. The sample is collected for each distance and glucose concentration is determined. A curve is constructed to provide a profile for the patient. The profile yields the optimal distance required for glucose extraction without resulting in visible skin damage, if such is desired. By placing the needle 20 as close as possible to the skin, blood or interstitial fluid can be extracted from the patient during the exposure of the patient to ultrasonic energy. The three-axis translation stage, available from Newport Corporation, Irvine Calif., can position the needle 20 at distances from the skin in increments of 10 µm. The quantity of glucose extracted as a function of distance of the needle 20 from the surface of the skin can be determined using this arrangement. At certain distances, biological fluids can be extracted without any skin damage visible to the naked eye.

It is preferred, but not required, that the needle 20 not penetrate the skin, but merely enhance transport of fluid by making the skin more permeable. In the case of extraction of interstitial fluid or blood from the skin, collection of fluid is typically effected by diffusion. However, artificial collection aids, such as vacuum, may also be used.

Other parameters, including displacement amplitude of the transducer, duty cycle of pulsed waves, and exposure duration may be varied to achieve optimal enhancement of transdermal transport. Typical values of these parameters are as follows: displacement amplitude: 5 µm to 100 µm; duty cycle: 10–100%; exposure duration: 1 to 5 minutes.

EXAMPLE II

The purpose of this example was to demonstrate that biological fluid can be obtained by means of a needle in transverse oscillation. The VCX 400 horn 12 was placed horizontally by means of a modified stand (not shown). A well positioner (not shown) (5 mm), which is a stand for supporting a well holder, was placed in proper alignment with the tip 18 of the VCX 400 horn 12. A needle 20 was attached to the tip 18 of the 13 mm probe 14 of the VCX 400 horn 12 by means of a modified screw 18. The needle 20 was aligned with the center of a well holder (not shown), which was attached to and supported by the well positioner. A well 30 was placed into the well holder and the tip 20b of the needle 20 was lowered until it was aligned with the bottom of the well 30. A modified well (5 mm diameter) was attached to the skin by means of adhesive. Saline solution (65 microliters) was placed in the well attached to the skin. The well 30 was placed into the well positioner and the needle 20 lowered as close as possible to the skin without touching. The region of skin subjected to the procedure was the top of the wrist of the left arm. The amplitude of the VCX 400 horn 12 was set at 15–20% (as desired). The VCX 400 horn 12 was turned on for a duration of one (1) minute. All fluid samples were extracted from the well and placed into HPLC vials. The previous five steps were repeated at one site nine more times. The presence of glucose on HPLC was measured. The flux was calculated. The results of this procedure are set forth in TABLE 1. For the data in TABLE 1, the amplitude of the VCX 400 horn 12 was set at 15%.

TABLE 1

| Sample number | Concentration of glucose (µg/mL) | Flux (with cell) (nmol/cm² · hr) | Flux (with needle) (nmol/cm² · hr) |
| --- | --- | --- | --- |
| 1 | 0 | 0.00 | 0.00 |
| 2 | 0 | 0.00 | 0.00 |
| 3 | 0.049 | 65.00 | 264.89 |
| 4 | 0.066 | 87.55 | 356.79 |

TABLE 1-continued

| Sample number | Concentration of glucose (µg/mL) | Flux (with cell) (nmol/cm² · hr) | Flux (with needle) (nmol/cm² · hr) |
| --- | --- | --- | --- |
| 5 | 0.339 | 449.71 | 1832.58 |
| 6 | 0.365 | 484.21 | 1973.14 |
| 7 | 0.305 | 404.61 | 1648.79 |
| 8 | 0.328 | 435.12 | 1773.12 |
| 9 | 0.865 | 1147.50 | 4676.06 |
| 10 | 1.304 | 1729.87 | 7049.23 |

No damage to the skin was observed. The flux values were relatively high. The value of flux (with cell) is based on the diameter of the orifice. The value of flux (with needle) is based on the diameter of the needle.

EXAMPLE III

The purpose of this example was to demonstrate sampling of glucose using a needle in transverse oscillation. The procedure of Example II was repeated, with the following exception:
Amplitude setting on VCX 400 horn: 16%
Diameter of needle: 0.76 mm; length of needle: 42 mm
The wattage delivered to the crystals (of the piezoelectric transducer) was recorded. The results of this procedure are set forth in TABLE 2.

TABLE 2

| Sample number | Concentration of glucose (µg/mL) | Flux (with cell) (nmol/cm² · hr) | Wattage |
| --- | --- | --- | --- |
| 1 | 0.115 | 153 | 36 |
| 2 | 0.679 | 901 | 37 |
| 3 | 1.029 | 1365 | 37 |
| 4 | 0.73 | 968 | 37 |
| 5 | 0.821 | 1089 | 38 |
| 6 | 1.286 | 1706 | 38 |
| 7 | 0.815 | 1081 | 37 |
| 8 | 1.095 | 1453 | 37 |
| 9 | 0.822 | 1090 | 38 |
| 10 | 0.686 | 910 | 38 |

No damage to the skin was observed. No pain was experienced by the patient.

EXAMPLE IV

The purpose of this example was to investigate the use of 1% sodium dodecyl sulfate with transverse oscillation. The procedure of Example II was repeated, with the following exceptions:
Amplitude setting on VCX 400 horn: 15%
Coupling medium: 1% sodium dodecyl sulfate in saline
Number of exposures: five exposures of one-minute duration at one location of the skin of one patient
Diameter of needle: 0.76 mm; length of needle: 42 mm
The wattage delivered to crystals (of the piezoelectric transducer) was recorded. The result of this procedure are set forth in TABLE 3.

TABLE 3

| Sample number | Concentration of glucose (µg/mL) | Wattage (W) |
| --- | --- | --- |
| 1 | 0.633 | 44 |
| 2 | 1.872 | 43 |
| 3 | 2.163 | 44 |

TABLE 3-continued

| Sample number | Concentration of glucose (μg/mL) | Wattage (W) |
|---|---|---|
| 4 | 1.856 | 44 |
| 5 | 2.651 | 44 |

Slight discomfort was experienced by the patient. Some skin irritation was observed after five exposures. No red dotting of the skin was observed.

EXAMPLE V

The purpose of this example was to determine the optimal distance for the highest flux of glucose. The procedure of Example II was repeated, with the following exceptions:
Number of exposures: three to five exposures of one-minute duration at one location of the skin of one patient
Length of needle: 21.5 mm; diameter of needle: not measured
Amplitude setting on VCX 400 horn: 3–5%
The wattage delivered to crystals (of the piezoelectric transducer) was recorded. The damage to the skin and the condition of the skin on the top of the wrist was recorded. For the three samples of Run number 1, the distance from the distal end of the needle to the surface of the skin was 100 μM and the amplitude setting for the VCX 400 horn was 3%. For the two samples of Run number 2, the distance from the distal end of the needle to the surface of the skin was 200 μM and the amplitude setting for the VCX 400 horn was 3%. For the two samples of Run number 3, the distance from the distal end of the needle to the surface of the skin was 250 μM and the amplitude setting for the VCX 400 horn was 5%. The results of this procedure are set forth in TABLE 4.

TABLE 4

| Run number | Sample number | Wattage (W) | Concentration of glucose (μg/mL) | Observations |
|---|---|---|---|---|
| 1 | 1 | — | 1.389 | White spot formed on skin; pain was experienced by patient |
| 1 | 2 | — | 2.855 | White spot formed on skin; pain was experienced by patient |
| 1 | 3 | — | 5.062 | White spot formed on skin; pain was experienced by patient |
| 2 | 1 | 19 | 3.256 | No skin damage was observed |
| 2 | 2 | 19 | 1.467 | No skin damage was observed |
| 3 | 1 | — | 3.999 | No skin damage was observed |
| 3 | 2 | — | 3.518 | No skin damage was observed |

EXAMPLE VI

The purpose of this example was to determine optimal conditions for high flux protocol. The procedure of Example II was repeated, with the following exceptions:
New well; small orifice
Amplitude setting on VCX 400 horn: 12–15%
Diameter of needle: 0.76 mm; length of needle: not measured
The distance of the distal end of needle from the surface of the skin was varied and the condition of the skin was recorded after exposure. The amplitude setting on the VCX horn for Runs number 1–12 was 15%. The amplitude setting on the VCX horn for Runs number 13–15 was 12%. The results of this procedure are set forth in TABLE 5.

TABLE 5

| Run number | Distance of distal end of needle from skin (μm) | Concentration of glucose (μg/ml) | Observation |
|---|---|---|---|
| 1 | 20 | 0.016 | A stinging sensation was experienced by the patient; skin was slightly damaged; no red dot was observed. |
| 2 | 40 | 1.091 | A stinging sensation was experienced by the patient; discomfort was experienced by the patient; a small indentation was observed on the skin. |
| 3 | 50 | 0.692 | No discomfort was experienced by the patient; no stinging sensation was experienced by the patient; a small raised area was observed on the skin. |
| 4 | 50 | 0.529 | No discomfort was experienced by the patient; no stinging sensation was experienced by the patient; a small raised area was observed on the skin. |
| 5 | 50 | 0.568 | No discomfort was experienced by the patient; no stinging sensation was experienced by the patient; a small raised area was observed on the skin. |
| 6 | 50 | 0.278 | No discomfort was experienced by the patient; no stinging sensation was experienced by the patient; a small raised area was observed on the skin. |
| 7 | 50 | 0.307 | No discomfort was experienced by the patient; no stinging sensation was experienced by the patient; a small raised area was observed on the skin. |
| 8 | 50 | 0.082 | No discomfort was experienced by the patient. |
| 9 | 50 | 0.370 | No discomfort was experienced by the patient. |
| 10 | 50 | 0.622 | A stinging sensation was experienced by the patient; skin was slightly damaged. |

TABLE 5-continued

| Run number | Distance of distal end of needle from skin (μm) | Concentration of glucose (μg/ml) | Observation |
|---|---|---|---|
| 11 | 60 | 2.454 | No discomfort was experienced by the patient. |
| 12 | 60 | 03.141 | Skin was serverly damaged. |
| 13 | 60 | 0.740 | No discomfort was experienced by the patient. |
| 14 | 60 | 0.868 | No discomfort was experienced by the patient. |
| 15 | 60 | 0.637 | A white spot was observed on the skin; no red dot was observed on the skin. |

Runs number 1 through 7 were carried out at one position on the skin of the patient. Runs number 8 through 10 were carried out at a second position on the skin of the patient. Runs number 11 through 15 were carried out at a third position on the skin of the patient.

EXAMPLE VII

The purpose of this example was to determine optimal conditions for high flux. The procedure of Example II was repeated, with the following exceptions:
Number of exposures: five exposures of one-minute duration at one location of the skin of each patient
Diameter of needle: 0.76 mm; length of needle: not measured
Volume of coupling medium: not measured
The condition of the skin was recorded after exposure. Runs number 1 through 10 were carried out at amplitude setting on the VCX horn of 10% at one position on the skin of the first patient. Runs number 11 through 20 were carried out at amplitude setting on the VCX horn of 10% at a second position on the skin of the first patient. Runs number 21 through 25 were carried out at amplitude setting on the VCX horn of 12% at a third position on the skin of the first patient. Runs number 26 through 30 were carried out at amplitude setting on the VCX horn of 10% at one position on the skin of a second patient. Runs number 31 through 35 were carried out at amplitude setting on the VCX horn of 12% at one position on the skin of the second patient. In Runs number 1–15, the distal end of the needle was 60 μm from the surface of the skin of the patient. In Runs number 16–35, the distal end of the needle was 65 μm from the surface of the skin of the patient. The results of this procedure are set forth in TABLE 6.

TABLE 6

| Run number | Distance of distal end of needle from from skin (μm) | Concentration of glucose (μg/ml) | Observation |
|---|---|---|---|
| 1 | 60 | 0.350 | No discomfort was experienced by the patient; loud noise came from needle and well. |
| 2 | 60 | 0.637 | No discomfort was experienced by the patient; loud noise came from needle and well. |
| 3 | 60 | 0.598 | No discomfort was experienced by the patient; loud noise came from needle and well. |
| 4 | 60 | 0.389 | No discomfort was experienced by the patient; loud noise came from needle and well. |
| 5 | 60 | 0.397 | No discomfort was experienced by the patient; loud noise came from needle and well. |
| 6 | 60 | 0.431 | No pain was experienced by the patient. |
| 7 | 60 | 0.682 | No pain was experienced by the patient. |
| 8 | 60 | 0.634 | No pain was experienced by the patient. |
| 9 | 60 | 0.492 | No pain was experienced by the patient. |
| 10 | 60 | 0.398 | No pain was experienced by the patient; after the 10th run, a drop of blood was obtained. |
| 11 | 60 | 0.272 | No discomfort was experienced by the patient; a very small red spot was observed on the skin. |
| 12 | 60 | 0.079 | No discomfort was experienced by the patient; a very small red spot was observed on the skin. |
| 13 | 60 | 0.128 | No discomfort was experienced by the patient; a very small red spot was observed on the skin. |
| 14 | 60 | 0.217 | No discomfort was experienced by the patient; a very small red spot was observed on the skin. |
| 15 | 60 | 0.251 | No discomfort was experienced by the patient; a very small red spot was observed on the skin. |
| 16 | 65 | 0.0 | No discomfort was experienced by the patient; no red spot was observed on the skin. |
| 17 | 65 | 0.0 | No discomfort was experienced by the patient; no red spot was observed on the skin. |
| 18 | 65 | 0.0 | No discomfort was experienced by the patient; no red spot was observed on the skin. |
| 19 | 65 | 0.0 | No discomfort was experienced by the patient; no red spot was observed on the skin. |

TABLE 6-continued

| Run number | Distance of distal end of needle from from skin ($\mu$m) | Concentration of glucose ($\mu$g/ml) | Observation |
| --- | --- | --- | --- |
| 20 | 65 | 0.0 | No discomfort was experienced by the patient; no red spot was observed on the skin. |
| 21 | 65 | 0.0 | No discomfort was experienced by the patient; no damaged to the skin was observed. |
| 22 | 65 | 0.0 | No discomfort was experienced by the patient; no damaged to the skin was observed. |
| 23 | 65 | 0.003 | No discomfort was experienced by the patient; no damaged to the skin was observed. |
| 24 | 65 | 0.428 | No discomfort was experienced by the patient; no damaged to the skin was observed. |
| 25 | 65 | 0.297 | No discomfort was experienced by the patient; no damaged to the skin was observed. |
| 26 | 65 | 0.079 | No damaged to the skin was observed; the apparatus produced a loud noise. |
| 27 | 65 | 0.501 | No damaged to the skin was observed; the apparatus produced a loud noise. |
| 28 | 65 | 0.462 | No damaged to the skin was observed; the apparatus produced a loud noise. |
| 29 | 65 | 0.488 | No damaged to the skin was observed; the apparatus produced a loud noise. |
| 30 | 65 | 0.417 | No damaged to the skin was observed; the apparatus produced a loud noise. |
| 31 | 65 | 0.276 | No damaged to the skin was observed; a slightly raised portion of the skin was noted. |
| 32 | 65 | 0.295 | No damaged to the skin was observed; a slightly raised portion of the skin was noted. |
| 33 | 65 | 0.297 | No damaged to the skin was observed; a slightly raised portion of the skin was noted. |
| 34 | 65 | 0.410 | No damaged to the skin was observed; a slightly raised portion of the skin was noted. |
| 35 | 65 | 0.376 | No damaged to the skin was observed; a slightly raised portion of the skin was noted. |

EXAMPLE VIII

The purpose of this example is to determine optimal conditions for high flux. The procedure of Example II was repeated, with the following exceptions:

Number of exposures: three to five exposures of one-minute duration at each location of the skin of the patient Amplitude setting on the VCX horn: 5%.

Needle: size 10/13 for Fine Bead Work from the DMC Corporation, South Kearny, N.J. 07032

The distance of the distal end of the needle from the surface of the skin was varied and the condition of the skin was recorded after exposure. The volume of coupling medium in the well was also varied. The results of this procedure are set forth in TABLE 7.

TABLE 7

| Run number | Distance of distal end of needle from skin ($\mu$m) | Volume of fluid in well ($\mu$l) | Concentration of glucose ($\mu$g/mL) | Observation |
| --- | --- | --- | --- | --- |
| 1 | 50 | 100 | 0.091 | No damage to the skin was observed; no pain was experienced by the patient. |
| 2 | 50 | 100 | 0 | No damage to the skin was observed; no pain was experienced by the patient. |
| 3 | 50 | 100 | 0 | No damage to the skin was observed; no pain was experienced by the patient. |
| 4 | 30 | 100 | 0 | No damage to the skin was visible; stinging was experienced by the patient. |
| 5 | 30 | 100 | 0.095 | No damage to the skin was visible; stinging was experienced by the patient. |
| 6 | 30 | 100 | 0.071 | No damage to the skin was visible; stinging was experienced by the patient. |

TABLE 7-continued

| Run number | Distance of distal end of needle from skin (μm) | Volume of fluid in well (μl) | Concentration of glucose (μg/mL) | Observation |
| --- | --- | --- | --- | --- |
| 7 | 40 | 80 | 0.146 | No damage to the skin was observed; no pain was experienced by the patient. |
| 8 | 40 | 80 | 0.138 | No damage to the skin was observed; no pain was experienced by the patient. |
| 9 | 40 | 80 | 0.151 | No damage to the skin was observed; no pain was experienced by the patient. |
| 10 | 40 | 80 | 0.167 | No damage to the skin was observed; no pain was experienced by the patient. |
| 11 | 40 | 80 | 0.125 | No damage to the skin was observed; no pain was experienced by the patient. |
| 12 | 30 | 70 | 0.235 | No damage to the skin was observed; no pain was experienced by the patient. |
| 13 | 30 | 70 | 0.406 | No damage to the skin was observed; no pain was experienced by the patient. |
| 14 | 30 | 70 | 0.295 | No damage to the skin was observed; no pain was experienced by the patient. |
| 15 | 30 | 70 | 0.102 | No damage to the skin was observed; no pain was experienced by the patient. |
| 16 | 25 | 70 | 0.252 | No pain was experienced by the patient; no damage to the skin was observed; a prickly feeling was experienced by the patient. |
| 17 | 25 | 70 | 0.332 | No pain was experienced by the patient; no damage to the skin was observed; a prickly feeling was experienced by the patient. |
| 18 | 25 | 70 | 0.233 | No pain was experienced by the patient; no damage to the skin was observed; a prickly feeling was experienced by the patient. |
| 19 | 25 | 70 | 0.168 | No pain was experienced by the patient; no damage to the skin was observed; a prickly feeling was experienced by the patient. |
| 20 | 25 | 70 | 0.165 | No pain was experienced by the patient; no damage to the skin was observed; a prickly feeling was experienced by the patient. |
| 21 | 20 | 70 | 0 | No pain was experienced by the patient; no damage to the skin was observed. |
| 22 | 20 | 70 | 0 | No pain was experienced by the patient; no damage to the skin was observed. |
| 23 | 20 | 70 | 0.055 | No pain was experienced by the patient; no damage to the skin was observed. |
| 24 | 20 | 70 | 0.091 | No pain was experienced by the patient; no damage to the skin was observed. |
| 25 | 20 | 70 | 0.243 | No pain was experienced by the patient; no damage to the skin was observed. |
| 26 | 15 | 70 | 1.020 | No pain was experienced by the patient; a very tiny red dot was observed on the skin; the samples obtained were yellowish in color. |
| 27 | 15 | 70 | 1.707 | No pain was experienced by the patient; a very tiny red dot was observed on the skin; the samples obtained were yellowish in color. |
| 28 | 15 | 70 | 0.785 | No pain was experienced by the patient; a very tiny red dot was observed on the skin; the samples obtained were yellowish in color. |

TABLE 7-continued

| Run number | Distance of distal end of needle from skin (μm) | Volume of fluid in well (μl) | Concentration of glucose (μg/mL) | Observation |
|---|---|---|---|---|
| 29 | 15 | 70 | 0.172 | No pain was experienced by the patient; a very tiny red dot was observed on the skin; the samples obtained were yellowish in color. |
| 30 | 15 | 70 | 0.176 | No pain was experienced by the patient; a very tiny red dot was observed on the skin; the samples obtained were yellowish in color. |
| 31 | 15 | 70 | 0.420 | No damage to the skin was observed; a slight tingling was experienced by the patient. |
| 32 | 15 | 70 | 0.435 | No damage to the skin was observed; a slight tingling was experienced by the patient: |
| 33 | 15 | 70 | 0.313 | No damage to the skin was observed; a slight tingling was experienced by the patient. |
| 34 | 15 | 70 | 0.356 | No damage to the skin was observed; a slight tingling was experienced by the patient. |
| 35 | 15 | 70 | 0.355 | No damage to the skin was observed; a slight tingling was experienced by the patient. |
| 36 | 15 | 70 | 0 | A slight prickly feeling was experienced by the patient; no damade to the skin was observed. |
| 37 | 15 | 70 | 0.202 | A slight prickly feeling was experienced by the patient; no damage to the skin was observed. |
| 38 | 15 | 70 | 0.245 | A slight prickly feeling was experienced by the patient; no damage to the skin was observed. |
| 39 | 15 | 70 | 0.175 | A slight prickly feeling was experienced by the patient; no damage to the skin was observed. |
| 40 | 15 | 70 | 0.213 | A slight prickly feeling was experienced by the patient; no damage to the skin was observed. |
| 41 | 15 | 70 | 0.466 | A slight prickly feeling was experienced by the patient; no damage to the skin was observed. |
| 42 | 15 | 70 | 0.519 | A slight prickly feeling was experienced by the patient; no damage to the skin was observed. |
| 43 | 15 | 70 | 0.387 | A slight prickly feeling was experienced by the patient; no damage to the skin was observed. |
| 44 | 15 | 70 | 0.240 | A slight prickly feeling was experienced by the patient; no damage to the skin was observed. |
| 45 | 15 | 70 | 0.183 | A slight prickly feeling was experienced by the patient; no damage to the skin was observed. |
| 46 | 15 | 70 | 0 | No damage to the skin was observed; some stinging was experienced by the patient. |
| 47 | 15 | 70 | 0 | some stinging was experienced by the patient. |
| 48 | 15 | 70 | 0 | No damage to the skin was observed; some stinging was experienced by the patient. |
| 49 | 15 | 70 | 0.133 | No damage to the skin was observed; some stinging was experienced by the patient. |
| 50 | 15 | 70 | 0.180 | No damage to the skin was observed; some stinging was experienced by the patient. |
| 51 | 15 | 70 | 0 | No damage to the skin was observed. |
| 52 | 15 | 70 | 0 | No damage to the skin was observed. |
| 53 | 15 | 70 | 0 | No damage to the skin was observed. |
| 54 | 15 | 70 | 0 | No damage to the skin was observed. |
| 55 | 15 | 70 | 0 | No damage to the skin was observed. |

EXAMPLE IX

The purpose of this example was to determine optimal conditions for high flux with respect to distance from the distal end of the needle to the surface of the skin. The distance from the distal end of the needle to the surface of the skin was varied from 30 μm to 160 μm. This example also demonstrated how the measurement of glucose concentration varied with the volume of coupling medium used for HPLC analysis. The procedure of Example II was repeated with the following exceptions:

Number of exposures: one to five exposures of one-minute duration at one location of the skin of the patient
Number of runs for each distance: one to five
Amplitude setting on the VCX horn: 5%
Needle: 0.4 mm diameter from DMC Corporation, South Kearny, N.J. 07032

The distance of the distal end of the needle from the surface of the skin was varied and the condition of the skin was recorded after the last exposure at each distance. The sample collected was also observed for any color changes. Two volumes of fluid were used: 10 μL and 5 μL. The results of this procedure are set forth in TABLE 8.

TABLE 8

| Run number | Distance of distal end of needle from skin (μm) | Concentration of glucose (μg/mL) using 10 μL of coupling medium | Concentration of glucose (μg/mL) using 5 μL of coupling medium | Skin condition using 10 μL of coupling medium | Skin condition using 5 μL of coupling medium |
|---|---|---|---|---|---|
| 1 | 30 | 5.276 | | yellow sample | |
| 2 | 30 | 43.15.5 | | red | |
| 3 | 65 | 3.618 | | | |
| 4 | 65 | 1.753 | | | |
| 5 | 65 | 1.399 | | blood spot | |
| 6 | 70 | 2.747 | | | |
| 7 | 70 | 2.336 | | | |
| 8 | 70 | 3.193 | | | |
| 9 | 70 | 6.507 | | yellow sample | |
| 10 | 70 | 4.164 | | blood spot | |
| 11 | 80 | 41.017 | | red sample | |
| 12 | 90 | 2.237 | | | |
| 13 | 90 | 3.85 | | | |
| 14 | 90 | 32.16 | | red sample | |
| 15 | 100 | 1.587 | | yellow | |
| 16 | 100 | 5.181 | | red spot | |
| 17 | 110 | 2.155 | | | |
| 18 | 110 | 3.184 | | | |
| 19 | 110 | 2.222 | | | |
| 20 | 110 | 10.183 | | tiny red dot | |
| 21 | 120 | 0.865 | 2.588 | | |
| 22 | 120 | 3.325 | 2.513 | | |
| 23 | 120 | 1.852 | 3.329 | | |
| 24 | 120 | 1.432 | 2.269 | red sample | |
| 25 | 120 | 9.862 | 3.348 | no damage | no damage |
| 26 | 130 | 5.119 | 0.028 | | |
| 27 | 130 | 2.101 | 4.415 | | |
| 28 | 130 | 1.445 | 11.517 | | |
| 29 | 130 | 1.122 | 5.899 | | |
| 30 | 130 | 0.933 | 4.114 | no damage | no damage |
| 31 | 140 | 0.389 | 2.611 | | |
| 32 | 140 | 0.733 | 2.107 | | |
| 33 | 140 | 0.856 | 3.169 | | |
| 34 | 140 | 0.943 | 2.525 | | |
| 35 | 140 | 0.625 | 1.911 | no damage | no damage |
| 36 | 150 | 0.727 | | | |
| 37 | 150 | 0 | | | |
| 38 | 150 | 0 | | | |
| 39 | 150 | 0 | | | |
| 40 | 150 | 0 | | no damage | |
| 41 | 160 | 0.949 | | | |
| 42 | 160 | 0.954 | | | |
| 43 | 160 | 1.032 | | | |
| 44 | 160 | 1.13 | | no damage | |
| 45 | 160 | 0.805 | | | |

The glucose concentration values set forth in TABLE 8 are undiluted values obtained from a HPLC instrument requiring a minimum analytical volume of 50 μL. The dilution factor for the runs with 10 μL of coupling medium was 6, i.e., 10 μL of coupling medium into 50 μL of saline. The dilution factor for the runs with 5 μL of coupling medium was 11, i.e., 5 μL into 50 μL.

The data show that when the distal end of the needle is at a distance of 120 μm away from the skin, fluid containing glucose can be extracted without resulting in skin damage. A volume of 5 μL of coupling medium can also be used to extract more than 2 μg per mL, which is the minimum concentration detectable by state-of-the art glucose sensors available for portable glucose sensing instruments.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for obtaining fluid from the body of a patient for diagnostic purposes, said method comprising the steps of:

(1) attaching a receptacle to the surface of the skin of a patient,
   (2) introducing an oscillation concentrator attached to an oscillation element into the receptacle,
   (3) positioning the oscillation concentrator at a desired distance from the surface of the skin,
   (4) activating the oscillation element to transversely oscillate the attached oscillation concentrator,
   (5) collecting the fluid after a specific period of time, and
   (6) analyzing the fluid for the presence of an analyte.

2. The method of claim 1, wherein said fluid is interstitial fluid.

3. The method of claim 1, wherein said fluid is blood.

4. The method of claim 1, wherein said receptacle contains a coupling medium.

5. The method of claim 4, wherein said coupling medium is a liquid.

6. The method of claim 1, wherein said oscillation concentrator is a needle having a proximal end and a distal end.

7. The method of claim 1, wherein the distal end of said needle is positioned at a distance ranging from about 0.1 $\mu$m to about 1000 $\mu$m from the surface of the skin.

8. The method of claim 1, wherein said oscillation concentrator is caused to oscillate at a frequency of $1 \times 10^2$ cycles per second to about $1 \times 10^9$ cycles per second.

9. The method of claim 1, wherein said oscillation element is an ultrasonic horn.

10. The method of claim 1, wherein said oscillation element is a piezoelectric transducer.

11. An apparatus for obtaining fluid from the body of a patient, said apparatus comprising:

(a) an oscillation concentrator having a proximal end and a distal end and having
   (b) an electromechanical transducer attached at the proximal end of said oscillation concentrator, said oscillation concentrator capable of oscillating in a transverse mode, said oscillation concentrator being of solid construction.

12. The apparatus of claim 11, wherein said electromechanical transducer is an ultrasonic horn.

13. The apparatus of claim 11, wherein said electromechanical transducer is a piezoelectric crystal.

14. The apparatus of claim 13, wherein said piezoelectric crystal is excited by voltage.

15. The apparatus of claim 14, wherein said voltage is applied via electrodes attached to said piezoelectric crystal, thereby causing the crystal to expand and contract in synchrony with the source of excitation, thereby resulting in vibration of said oscillation concentrator.

16. The apparatus of claim 15, wherein said piezoelectric crystal transfers vibration to said oscillation concentrator, thereby causing freely transverse displacement of the distal end of said oscillation concentrator.

17. The apparatus of claim 11, wherein said oscillation concentrator is a needle having a proximal end and a distal end.

18. An apparatus for obtaining fluid from the body of a patient, said apparatus comprising:

(a) an oscillation concentrator having a proximal end and a distal end and having
   (b) an electromechanical transducer attached at the proximal end of said oscillation concentrator, said oscillation concentrator capable of oscillating in a transverse mode, wherein said oscillation concentrator is immersed in a reservoir containing a coupling medium in such a manner that the coupling medium is in contact with the surface of human or animal skin.

19. The apparatus of claim 18, wherein the coupling medium is a liquid.

* * * * *